United States Patent [19]

Nexo et al.

[11] 4,247,773

[45] Jan. 27, 1981

[54] METHOD FOR QUANTITATIVELY DETERMINING FAT IN A FAT-CONTAINING SAMPLE

[75] Inventors: Sten A. Nexo, Birkerod; Henrik R. Andersen, Kastrup, both of Denmark

[73] Assignee: A/S N. Foss Electric, Denmark

[21] Appl. No.: 60,411

[22] Filed: Jul. 25, 1979

[30] Foreign Application Priority Data

Dec. 6, 1978 [DK] Denmark ............... 5516/78
Jul. 3, 1979 [DK] Denmark ............... 2814/79

[51] Int. Cl.³ .................................................. G01J 1/00
[52] U.S. Cl. .................................... 250/339; 250/341; 250/343
[58] Field of Search ............... 250/338, 339, 340, 341, 250/343, 344, 345; 356/432, 435, 436, 442

[56] References Cited

U.S. PATENT DOCUMENTS

| | | | |
|---|---|---|---|
| 3,161,768 | 12/1964 | Goulden | 250/339 |
| 3,803,384 | 4/1974 | Braunlich | 250/345 |
| 3,839,633 | 10/1974 | McKenna et al. | 250/343 |
| 3,972,625 | 8/1976 | Takahasi et al. | 356/435 |
| 4,076,983 | 2/1978 | Hopkins et al. | 250/341 |

FOREIGN PATENT DOCUMENTS 2344986 3/1975 Fed. Rep. of Germany .
2355565 5/1975 Fed. Rep. of Germany .
989617 of 1965 United Kingdom .

OTHER PUBLICATIONS

Goulden, J. D. S.: J. Sci. Food Agric. 7, p. 609, 1956.
Goulden, J. D. S.: Nature, p. 905, 1961.
Goulden, J. D. S.: J. Dairy Res., 31, p. 273, 1964.
Goulden, J. D. S.: J. Soc. Dairy Technol. 17, p. 28, 1964.
Grappin, R., Jeunet, R.: LeLait, p. 324, 1972.
Grappin, R., Jeunet, R.: LeLait, p. 498, 1976.
John Shields Thesis at U. of York, 1975.

*Primary Examiner*—Davis L. Willis
*Attorney, Agent, or Firm*—Hubbell, Cohen, Stiefel & Gross

[57] ABSTRACT

Fat in a fat-containing sample, in particular a milk sample, is determined quantitatively by infrared absorption technique, using as sample waveband a band characteristic to carbon-hydrogen bonds, instead of the conventional triglyceride carbonyl band. This avoids the dependency of the measured result on the fat composition of the sample. Influences from other components in the sample are compensated for. A preferred method uses double wavelength determination, with sample wavelength in the interval from 3.475 to 3.51 μm and reference wavelength in the range between 3.51 and 3.60 μm.

15 Claims, 1 Drawing Figure

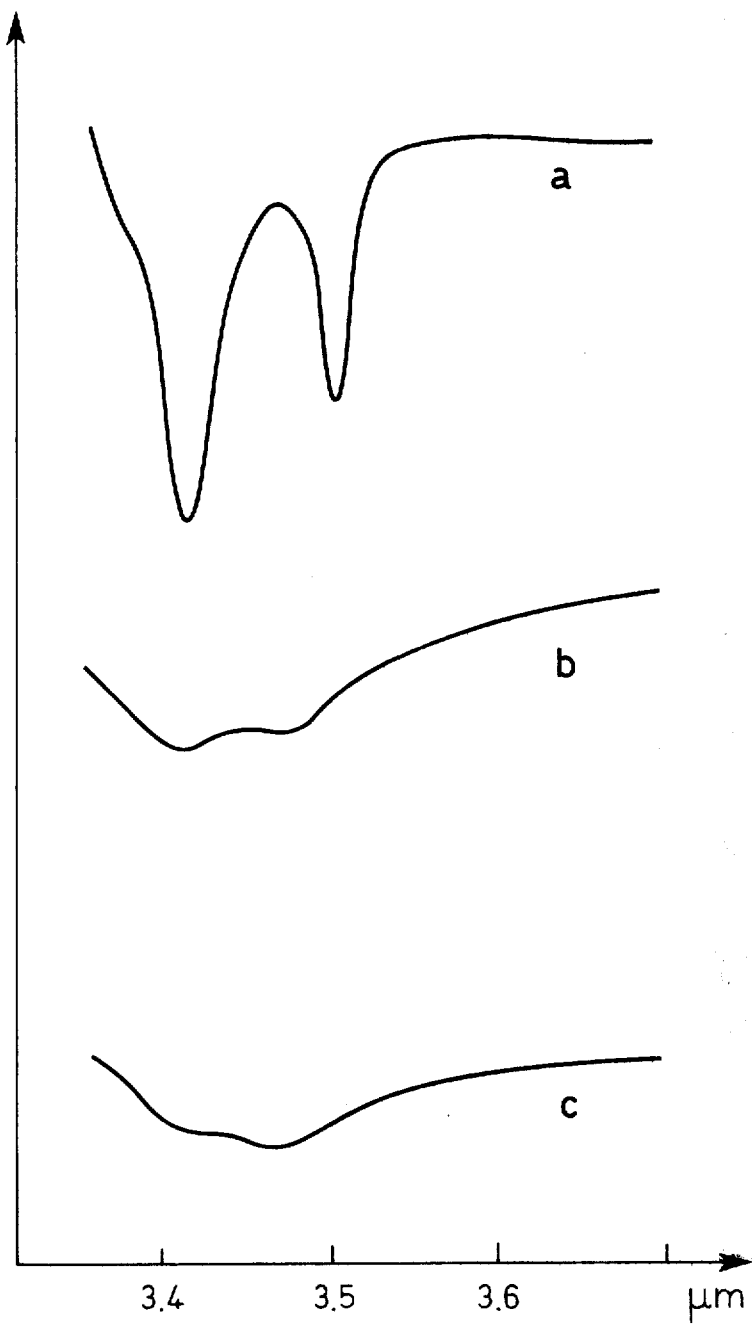

METHOD FOR QUANTITATIVELY DETERMINING FAT IN A FAT-CONTAINING SAMPLE

BACKGROUND OF THE INVENTION

The present invention relates to a method for quantitative determination of the fat content of a fat-containing sample.

It is known to determine the fat content in fat-containing samples, in particular milk samples, by infrared absorption techniques. Infrared absorption methods and apparatus for determining fat content in milk are described e.g. by Goulden, J. D. S.: British Pat. No. 989,617, Goulden, J. D. S.: J. Sci. Food Agric., 7, 609 (1956), Goulden, J. D. S.: Nature, 191, 905 (1961), Goulden, J. D. S.: J. Dairy Res., 31, 273 (1964), Goulden, J. D. S.: J. Soc. Dairy Techn., 17, 28 (1964), Grappin R., Jeunet R.: Le Lait, 52, 325 (1972), in a thesis by John Shields submitted for the degree of Bachelor of Philosophy at the University of York, November 1975, by Grappin R., Jeunet R.: Le Lait, 56, 498 (1976), Grappin R., Jeunet R.: Le Lait, 558, 1-16, (1976), in U.S. Patent Application No. 3,161,768 and U.S. Patent Application No. 931,621.

The principle of the infrared fat determination is based on measuring the absorption of the infrared light in the triglyceride carbonyl band at 5.73 $\mu$m. In this waveband, the spectral influence of other components present in the sample, in particular protein and lactose, is low as they show no absorption, and hence, the absorption measured in the said band gives a good measure of the number of fat molecules in the sample.

The accuracy of the milk fat determination by the infrared method is of decisive importance to the usefulness of the method, as the measured results are used as basis for e.g. milk payment. It has been found, however, that the weight percentage of fat determined by the infrared method varies with varying chemical composition of the fat, for example due to seasonal variations, variations in feedstuff and breed of the milking cows, and such variations present a serious problem limiting the usefulness of the infrared absorption method and the acceptability of the method by the authorities in certain territories. Variations in fat composition require a frequent calibration of infrared milk analyzers against the chemical standard methods.

SUMMARY OF THE INVENTION

According to the present invention, it has now been found that an accurate quantitative infrared absorption determination of fat in fat-containing samples can be obtained without the above-mentioned dependency on the fat composition and the disadvantages incurred thereby.

According to the present invention, the fat content of a fat-containing sample is determined quantitatively by determining the infrared absorption of the sample in a waveband characteristic to saturated carbon-hydrogen bonds. To the applicants' best knowledge, it has never previously been suggested to quantitatively determine the fat content of a sample on the basis of the infrared absorption of the sample in a waveband characteristic to saturated carbon-hydrogen bonds. From absorption curves shown in some of the above-mentioned references, for example Goulden, J. D. S.: J. Sci. Food Agric., 7, 609 (1956), it was known that butter-fat does, of course, absorb in a waveband characteristic to saturated carbon-hydrogen bonds, for example a characteristic peak around 3.5 $\mu$m, but none of the references contain any suggestion of using this band for quantitative fat determination; on the contrary, they recommend the above-mentioned triglyceride carbonyl band for this purpose. Also, for example Goulden, J. D. S.: Nature, 191, 905 (1961) teaches that the absorption peak of 5.8 is preferred because the mean fat globule diameter of homogenized milk samples is about 1 $\mu$m, so that, to minimize scattering effects, wavelengths greater than 5 $\mu$m would be selected.

According to the invention, it has surprisingly been found that in spite of the fact that other organic components in a fat-containing sample contain hydrogen-carbon bonds and, therefore, influence the infrared absorption determined in a waveband characteristic to saturated carbon-hydrogen bonds, the accuracy (as compared to the standard chemical determination) which is obtainable by determining the fat content on the basis of the infrared absorption in the waveband characteristic to saturated carbon-hydrogen bonds can be made much better than when working in the above-mentioned triglyceride carbonyl band, and that undesired influences from other components in the sample affecting the measuring result can be effectively compensated for. The infrared absorption measured in a waveband characteristic to carbon-hydrogen bonds is related to both the size and the number of fat molecules in the sample, as the number of carbon-hydrogen bonds in the fat molecule increases substantially proportionally with the molecule size. Therefore, the method of the invention permits an accurate fat determination obviating the above-mentioned error incurred by variations in fat composition due to for example seasonal variation, thus obviating the need for frequent calibration of the apparatus.

Another advantage of the method of the invention is that free fatty acids formed in the sample during storage after sampling are (correctly) included in the fat determination as they contribute to the absorption in the carbon-hydrogen bond waveband in quantitatively substantially the same manner as the fat molecules, which is in contrast to the known method measuring the triglyceride carbonyl absorption band in which such free fatty acids are not measured. On the other hand, lactic acid present in the sample (for example as microbial deterioration product of carbohydrates in the sample due to unsuitable storage conditions) has been found not to contribute significantly to the fat content determined by the method according to the present invention. (The carbonyl band of lactic acid is sufficiently close to the triglyceride carbonyl band to interfere strongly with the known fat determination method and give an incorrect contribution to the fat content measured.)

BRIEF DESCRIPTION OF THE DRAWING

The drawing shows characteristic transmission spectra in the wavelength range from 3.3 to 3.6 $\mu$m for (a) fat, (b) protein + lactose and (c) lactose.

DETAILED DESCRIPTION OF THE INVENTION

A preferred carbon-hydrogen bond IR absorption wavelength band used according to the invention is the double band around 3.45 $\mu$m (from 3.35 to 3.51 $\mu$m), typically a band in the range between 3.475 and 3.51 $\mu$m, e.g. a band having a center wavelength of 3.49 $\mu$m.

Known apparatus for IR determination of fat, e.g. milkfat, uses either a single wavelength dual cuvette or a double wavelength single cuvette measurement. The double wavelength system has several advantages, inter alia that it balances out variations in water or solvent content in the sample, compensates for scatter effects in the sample, and compensates for accumulated dirt in the cuvette. Because of these better compensation possibilities, it is preferred to use a double wavelength system in the method of this invention, and such a double wavelength system is described in detail in the above-mentioned dissertation by John Shields and is mentioned in the above-mentioned 1976 article by R. Grapin and R. Jeunet. A recent development in the double wavelength systems is a double wavelength single cuvette single beam apparatus as described in U.S. Patent Application Ser. No. 931,621 of Aug. 7, 1978.

When utilizing the double wavelength principle in the method of the invention, the determination of the absorption in the band characteristic to carbon-hydrogen bonds is accompanied by a simultaneous absorption determination at an adjacent reference wavelength, the reference wavelength being preferably in the range between 3.51 and 4.00 $\mu$m, especially in the range between 3.51 and 3.60 $\mu$m, e.g. a band having a center wavelength of 3.56 $\mu$m, and the read-out of the apparatus is calculated from the ratio between the sample wavelength energy and the reference wavelength energy. One problem which may interfere with the known double wavelength method is that the scatter compensation may be insufficient if the fat globules to be measured have not been homogenized to a sufficiently small size, this being due to shifts in refractive index over the absorption band. When working in the above-mentioned measuring band around 3.45 $\mu$m and in the above-mentioned reference band between 3.51 and 3.60 $\mu$m, there is no significant shift in refractive index, and hence, a satisfactory scatter compensation is obtained.

The infrared waveband in which the fat determination in the method of the invention is performed is obtained by means of a wide band infrared light emitter, the light of which is passed through a suitable monochromator means, for example an optical interference filter, a prism, or a grating monochromator. The half power bandwidth of the infrared light in the interval characteristic to carbon-hydrogen bonds is preferably about 35 nm, but it has also been found possible to use a filter of much larger bandwidth and still obtain excellent results. The bandwidth of the infrared light for the reference measurement is not particularly critical and may be for example 20–100 nm or even larger.

The sample on which the fat determination is performed is preferably a liquid sample, in principle either a fat-containing solution in a suitable solvent or an aqueous fat emulsion. The sample may be prepared from any material, the fat content of which is to be determined, for example from meat, milk powder, cheese, ice cream, sour milk products, etc. by suitable sample preparation techniques known per se aiming at presenting the sample in liquid form. Whether the sample is milk or a milk product or any other product, the sample preparation should be such that the sample, when introduced in the cuvette of the apparatus, does not contain particles which will be capable of disturbing the IR measurement by scatter or absorption effects, and this means that the average particle diameter in a sample in the form of a suspension or emulsion should typically be below 2 $\mu$m, preferably below 1,2 $\mu$m, or, expressed more suitably by average particle volume, at the most $14 \times 10^{-9}$ $\mu$liter, preferably at the most $4 \times 10^{-9}$ $\mu$liter.

When the sample is a milk product, this is suitably obtained by homogenizing the milk sample in a manner known per se, suitably in a homogenizer built into the IR measuring apparatus.

In the above-mentioned wavelength range of 3.35 to 3.51 $\mu$m, two major components in milk, that is protein and lactose, show significant infrared absorption, but it has been found that the interference from these components is sufficiently small to be removable by suitable compensation. The drawing shows characteristic transmission spectra in the wavelength range from 3.3 to 3.6 $\mu$m for (a) fat (a double beam balance spectrum of a 3.5% fat milk sample against a skim milk with the same lactose and protein content), (b) protein + lactose (double beam balance spectrum of skim milk against water), and (c) lactose (double beam balance spectrum of 5% lactose solution in water against water).

The path length in all three cases was 37 $\mu$m. It will be noted that the curves for lactose + protein and for lactose show that also these components absorb in the wavelength range in question. The peak around 3.5 $\mu$m is a preferred peak because it is sufficiently displaced from the absorption peaks of protein and lactose to permit measurement of the fat absorption with relatively small influence from these other components and sufficiently remote from the water band to give a good water balance.

As mentioned above, influence from protein and lactose in milk can be sufficiently compensated for in the method of the invention. It is noted that in such determinations on fat-containing multi-component samples, in particular suspensions or emulsions, milk being taken as an example for such an emulsion in the following explanation, there are three main reasons for cross interferences between the components (these being fat, protein, lactose and water in the case of milk):

(1) Water displacement effects which arise due to the fact that the presence of milk components will displace more or less water with the result that the infrared absorption as measured will chance depending on the water balance of the system. These water displacement effects are normally the dominating effects in infrared milk analysis. The influence from fat and lactose depends directly on their weight concentrations, while the protein influence also depends on the ratio of soluble to suspended proteins since they will displace water differently.

(2) The spectral influences due to the above-mentioned infrared absorption by protein and lactose in the wavelength selected will interfere with the fat measurement. The absorption due to fat and lactose in a milk sample will largely depend on the number of molecules per volume when only one characteristic bond per molecule is responsible (fat influence on lactose) and thus on the concentration as determined by infrared absorption. If many bonds per molecule give the effects (such as fat influence on protein and lactose influence on fat and protein), the effects will mainly depend on the weight concentrations of the single components.

(3) Effects ascribable to variations in specific gravity may become of importance, because for protein and lactose, only the number of molecules in a certain volume is determined by the IR absorption measurement, which means that the derivation of a weight percent signal requires knowledge of the specific gravity of milk. In other words, this derivation will be altered by components which have a specific gravity that differs from that of average milk and which displace more or less milk than they weigh. In this connection, fat will anyway give a rather small effect since it displaces almost the same mass as it weighs. Fat and lactose influences will depend directly on their concentrations, whereas protein effects will depend on the composition of the protein as mentioned under 1). These effects, however, are generally small.

Influences from other components in the sample having saturated carbon-hydrogen bonds, in other words the compensation for protein and lactose in the case of milk, may be performed on the basis of a predetermined relationship between the concentration of said components and their interference with the fat measurements. Such relationships are suitably determined by multiple linear regression based on empirical data or by checking with "artificial" samples prepared by adding a known amount of one of the disturbing components to a sample to determine the degree of interference. In principle, the concentration of the protein and of the lactose may be determined in any suitable way, but in a preferred embodiment, the protein and lactose determinations are performed by infrared absorption technique in the same apparatus as the fat determination, in the manner as described in the above-mentioned U.S. Patent Application and the above-cited literature. In practice, a suitable way of handling the composition is to set up a system of three equations with three unknowns, the unknowns being the corrected contents for fat, lactose, and protein content, respectively, and the knowns being the measured values of these respective contents, the coefficients of the equation system being determined in advance on a number of calibrated natural or "artificial" milk samples. Suitably, the instrument used for the fat determination is equipped with adequate computing facilities such as an analogue computer or a microprocessor for performing the necessary calculations.

One particular aspect of the invention is based on the fact that light in the band from 3 to 4 μm can be obtained from a common light source such as an ordinary light bulb, and that the cuvette material for use in this wavelength region is not critical and may consist of for example water-free glass. This opens up the possibility of manufacturing low cost infrared fat determination apparatus for situations where the necessary accuracy of the correction for other components can be performed with fixed constants adapted to the particular measuring situation, of the conventional IR determinations of for example proteins and lactose can be replaced, for correction purposes, with signals derived in any other way which does not require the use of wavelengths above 4 μm. Especially in situations where routine fat determinations are performed on samples which are known to have substantially constant contents of interfering components, typically milk samples in which the protein and lactose variation is known to be low, it may be sufficient to measure only fat and perform a standardized correction for the other components.

EXAMPLE 1

The instrument used was a Milko-Scan 104 from A/S N. Foss Electric, Denmark. The principle of this instrument is described in the above-mentioned U.S. Patent Application Serial No. 931,621 (and German Patent Application No. P 28 38 706.6). However, the apparatus was modified by inserting, instead of the two standard water filters, one filter having a bandwidth of 75 nm around a center wavelength of 3.478 μm (sample filter) and another filter having a bandwidth of 75 nm around the center wavelength of 3.580 μm (reference filter). With this set of filters, the correction equation had in advance been found in the manner described above to be $F = F_{uc} - 0.10 P_{uc} - -0.23 L_{uc}$ where F designates the true fat readout, $F_{uc}$ designates the uncorrected fat readout, $P_{uc}$ designates uncorrected protein content and $L_{uc}$ designates uncorrected lactose content, the contents being in weight by weight units.

30 milk samples (herd milk, skim milk, mixtures thereof and mixtures of herd milk with cream, all of different origin) with fat content varying from 0.1 percent by weight to 7 percent by weight, preserved by addition of 0.05 percent of potassium dichromate and heated to 40° C., were analyzed in the apparatus. The fat content of each sample was also measured according to the Röse-Gottlieb standard method by double determination. The protein and lactose used for the cross-correction were measured in the same apparatus, and the processing of the cross-correction equation was performed in the analogue computer of the apparatus. The apparatus also determined the fat content by measuring the infrared absorption in the triglyceride carbonyl waveband (not according to the invention) in the normal way. Comparisons against the chemical determinations showed a standard deviation of 0.073 weight percent of fat for the carbonyl band determination and standard deviation of 0.025 weight percent of fat for the carbon-hydrogen bond determination according to the invention. The standard deviation on the carbonyl band determination was high due to variation in the fat composition, whereas the standard deviation on the carbon-hydrogen bond waveband determination approached the reproducibility of the standard method, in spite of the high variation in the fat composition of these samples.

With the standard two stage spring-loaded ball valve homogenizer of the Milko-Scan 104 (first stage about 120 atmospheres, second stage about 50 atmospheres, resulting in an average particle size of about 0.9–1 μm), it was not possible to see any significant variations in the fat readout when performing external homogenizations at various pressures in the range from 0 to 250 atmospheres on a raw milk sample with a fat content of about 5 percent by weight.

EXAMPLE 2

On the same instrument as described in Example 1, 22 boxes of each 48 herd milk samples delivered to various Dutch dairies were subjected to fat determination using both the carbonyl band determination at 5.7 μm and the carbon-hydrogen bond band determination at 3.478 μm (in the below table abbreviated to "3.5 μm"). The apparatus also measured the protein and lactose contents of the samples and performed the cross-correction in the same manner as described in Example 1. All the determinations were performed as double determinations. Concomitantly with this, the fat percentages of the samples were measured by double determinations according to the standard Gerber method.

The results appear from the below table which contains information about the standard deviation from the Gerber method (SD) and the mean deviation (Δ) from the Gerber method. From the dairies, the milk samples were preserved by addition of preservative tablets (potassium dichromate as preservative formulated with a high amount of NaCl). It was discovered that there was a difference in routine between the dairies in that some of the dairies used 1 salt tablet and others used 2 preservative tablets. The means deviations given in the below table are corrected for this difference.

TABLE.

| Dairy | Fat, 5.7 μm Δ | SD | Fat, 3.5 μm Δ | SD | Regression of deviation vs. refractive index (number of samples 161) 5.7 μm | 3.5 μm |
|---|---|---|---|---|---|---|
| 1 | +0.028 | 0.051 | −0.091 | 0.026 | y = −0.077x + 3.28  r = −0.74 | y = −0.013x + 0.56  r = −0.25 |
| 2 | +0.028 | 0.053 | −0.074 | 0.026 | y = −0.069x + 2.78  r = −0.92 | y = −0.016x + 0.64  r = −0.50 |
| 3 | +0.042 | 0.055 | −0.066 | 0.029 | y = −0.078x + 3.36  r = −0.82 | y = −0.008x + 0.28  r = −0.18 |
| 4 | +0.31 | 0.058 | −0.076 | 0.031 | y = −0.092x + 3.91  r = −0.91 | y = −0.021x 0.77  r = −0.52 |
| 5 | +0.069 | 0.036 | −0.060 | 0.029 | y = −0.03x + 1.38  r = −0.56 | y = +0.022x − 0.99  r = +0.52 |
| 6 | +0.036 | 0.055 | −0.067 | 0.031 | y = −0.080x + 3.44  r = −0.72 | y = −0.002x − 0.16  r = −0.033 |
| 7 | +0.047 | 0.045 | −0.049 | 0.025 | | |
| 8 | +0.071 | 0.034 | −0.046 | 0.025 | | |
| 9 | +0.045 | 0.052 | −0.057 | 0.031 | | |
| 10 | +0.080 | 0.040 | −0.072 | 0.034 | | |
| 11 | +0.059 | 0.043 | −0.053 | 0.025 | | |
| 12 | +0.067 | 0.040 | −0.048 | 0.022 | | |
| 13 | +0.048 | 0.049 | −0.057 | 0.028 | | |
| 14 | +0.059 | 0.056 | −0.055 | 0.026 | | |
| 15 | +0.040 | 0.038 | −0.063 | 0.030 | | |
| 16 | +0.052 | 0.068 | −0.066 | 0.047 | | |

SD of Δ, 5.7 μm: 0.016
SD of Δ, 3.5μm: 0.012

When all the above regression data for each band are combined in one regression equation, the following regression equations are obtained:

5.7 μm: $y = -0.658x + 2.806$
$r = -0.760$ 3.5 μm: $y = -0.0076x + 0.32$
$r = -0.188$

It will be noted from the above data that the mean deviation from the Gerber method is subject to less variation when measuring at 3.5 μm than when measuring at 5.7 μm (standard deviation 0.012 instead of 0.016). This obviates the necessity of recalibrating the instrument in connection with each change of dairy in the sample material. In the 5.7 μm measurement, such recalibration was often found necessary because of the difference in composition owing to variations in the local conditions. It is also noted that the standard deviation from the Gerber method when measuring at 3.5 μm is much smaller than when measuring at 5.7 μm. From the regression of deviation versus refractive index, it will be noted that the dependency of the 3.5 μm method of the refractive index is very much smaller than when measuring at 5.7 μm. The very low correlation coefficient and slope show that the deviation from the Gerber method is virtually independent of the refractive index, which is a most satisfactory result.

It is noted that the values stated in the table comprise variations deriving from varying salt concentrations due to different degree of filling of the sample bottles, and that it is comtemplated that the standard deviation of 0.012 percent on the mean deviations between the method of the invention and the Gerber method will probably be even smaller when the dependency on the salt concentration is minimized by means of optical filters which are specifically adapted to the purpose, i.e., optical filters which have more narrow bandwidths of the order of 35 nm.

In order to determine the influence of the age of the sample on the measurement performed according to the present invention, fresh delivered milk from 10 farms was preserved by means of four different preservation agents: mercury chloride, potassium dichromate, sodium azide, and a mixture of mercury chloride and sodium azide. The resulting 25 sets of each 40 samples were stored at 7° C. and 14° C. and were investigaged with intervals over a period of 25 days. The same determinations as mentioned above were performed on the samples, all of the determinations were made as double determinations.

For each of the parameters, the average over each of the four groups of 10 samples containing the same preservation agent was calculated, and the mean results were plotted in time diagrams.

It was found that the Gerber determination showed no particular tendency, but on the other hand showed a considerable variation in the results (peak to peak variation about 0.04 percent). The measurement at 5.7 μm showed less day-to-day variation, but no clear tendency over the 25 days.

The measurements at 3.5 μm according to the invention showed a very small day-to-day variation and a very small increase in tendency of the order of 0.02 percent over 25 days.

The most interesting result of this test was that the very few samples which showed a very high content of free fatty acids, also gave rise to a considerable decrease in the determination at 5.7 μm (about 0.45 percent), which is in accordance with previous experience, while the only change at 3.5 μm was an increase of 0.04 percent, which is in accordance with the theory. In other words, also in this regard, the method of the invention shows a very considerable improvement over the prior art.

We claim:

1. A method for quantitative measurement of fat in a fat-containing sample by an infrared absorption technique, comprising transmitting infrared light through the sample, determining the infrared absorption of the sample in a waveband characteristic of saturated carbon-hydrogen bonds, and selectively, quantitatively assessing the fat content of the sample on the basis of said determination.

2. A method as claimed in claim 1 in which the wavelength at which the IR absorption characteristic to carbon-hydrogen bonds is determined is a wavelength in the band from 3.35 to 3.51 $\mu$m.

3. A method as claimed in claim 1 in which the bandwidth of the infrared light in the interval characterictic to carbon-hydrogen bonds is about 35 nm.

4. A method as claimed in claim 3 in which the wavelength range of the infrared light in the interval characteristic to carbon-hydrogen bonds is from 3.475 to 3.51 $\mu$m.

5. A method as claimed in claim 1 in which the infrared absorption is determined at two different wavelengths, one in the band characteristic to carbon-hydrogen bonds, the other one being an adjacent reference wavelength.

6. A method as claimed in claim 5 in which the reference wavelength is in the range between 3.51 and 4.00 $\mu$m.

7. A method as claimed in claim 6 in which the reference wavelength is in the range between 3.51 and 3.60 $\mu$m.

8. A method as claimed in claim 1 in which undesired influences from other components in the sample affecting the measured result are compensated for.

9. A method as claimed in claim 8 in which undesired influences from other saturated carbon-hydrogen bond-containing components in the sample are compensated for.

10. A method as claimed in claim 8 in which the compensation for undesired influences from other components in the sample is performed by determining the concentration of the said other components and correcting for the influence thereof on the measured results, the correction being performed on the basis of a predetermined relationship between the concentration of said components and their influence on the measured results.

11. A method as claimed in claim 1 in which the sample is a liquid sample.

12. A method as claimed in claim 11 in which the sample is an aqueous fat emulsion.

13. A method as claimed in in claim 12 in which the sample is milk or a milk product.

14. A method as claimed in claims 12 in which the average fat globule volume in the emulsion is at the most $14 \times 10^{-9}$ $\mu$liter.

15. A method as claimed in claim 14 in which the average fat globule volume in the emulsion is at the most $4 \times 10^{-9}$ $\mu$liter.

* * * * *